(12) United States Patent
VanDam

(10) Patent No.: US 10,314,529 B2
(45) Date of Patent: Jun. 11, 2019

(54) VOCAL MONITORING AND BIOFEEDBACK DEVICE

(71) Applicant: Washington State University, Pullman, WA (US)

(72) Inventor: Mark VanDam, Spokane, WA (US)

(73) Assignee: WASHINGTON STATE UNIVERSITY, Pullman, WA (US)

( * ) Notice: Subject to any disclaimer, the term of this patent is extended or adjusted under 35 U.S.C. 154(b) by 286 days.

(21) Appl. No.: 15/354,288

(22) Filed: Nov. 17, 2016

(65) Prior Publication Data
US 2018/0132779 A1    May 17, 2018

(51) Int. Cl.
*A61B 5/00* (2006.01)
*G09B 19/04* (2006.01)
*A61F 5/58* (2006.01)

(52) U.S. Cl.
CPC .......... *A61B 5/4803* (2013.01); *A61B 5/7235* (2013.01); *A61F 5/58* (2013.01); *G09B 19/04* (2013.01); *A61B 5/486* (2013.01); *A61B 5/6822* (2013.01); *A61B 2562/0204* (2013.01); *A61B 2562/0219* (2013.01)

(58) Field of Classification Search
CPC .... A61B 2562/0204; A61B 2562/0219; A61B 5/4803; A61B 5/486; A61B 5/6822; A61B 5/7235
See application file for complete search history.

*Primary Examiner* — Christine H Matthews
(74) *Attorney, Agent, or Firm* — W & C IP

(57) ABSTRACT

A vocal dosimeter receives a first set of sensor data as sensor outputs through a sensor array including an acoustic sensor, a piezoelectric sensor, and an accelerometer. The dosimeter generates normalized sensor waveforms by filtering for an amplitude range from the quadratic mean of each individual raw sensor waveform through control of a first band-pass filter, and operates laryngeal activity detection to configure a vocalization filter with a vocalization threshold within a vocalization analysis window. A feedback control is generated in response to identifying a statistically similar vocalization amplitude in a vocal characteristic database.

15 Claims, 13 Drawing Sheets

VOCAL MONITORING AND BIOFEEDBACK DEVICE

BACKGROUND

Pathological speech affects millions of Americans. It is characterized by variable speech rate, segmental production errors, including reduced vowel articulation space, reduced respiratory function for speaking, voice problems (hoarseness, breathiness, tremulousness, amplitude perturbation/shimmer, irregular pitch/jitter), reduced prosodic variability, and reduced amplitude/loudness.

Management and treatment of pathological speech typically includes face-to-face therapy from a speech-language pathologist or a similar clinician. Many with pathological speech issues do not receive treatment due to cost or other barriers to services. As a result, reduction in quality of life have been well-documented, affecting the ability to maintain and be involved in conversations and limiting the ability to communicate wants and needs. This leads to restricted social and personal lives contributing to depression, reduced access to healthcare and healthcare professionals, and reduced access to independent living especially for seniors.

Regaining vocal presence has been shown to be pivotal in regaining the ability to effectively communicate in a healthy lifestyle. There are two principal problems with the current state of treatment for pathological voice problems. First, there is a poor understanding of the natural, systematic mechanisms underlying speech production in situ. Scientific knowledge of vocal pathology is almost entirely based on clinical and anecdotal descriptions. Modern (clinical) science is ever more firmly rooted in empirical evidence as the basis for intervention. That empirical basis is currently unknown.

Second, intervention or therapy (regardless of whether it addresses an accurate description of the problem) has many barriers to real-world application including financial burden, availability of technology, ease of use, demonstrated real-time and generalized effectiveness, and ecological portability (here, wearability).

Known devices for training voice patterns include those disclosed in US Patent Publication No. 20140330557 A1; and U.S. Pat. No. 9,381,110B2. Prior devices rely on an accelerometer and a manually set threshold range to indicate vocal activity. Sensor data from an accelerometer is sent to a preamplifier and a bandpass filter to apply a gain of 2000 and limit the frequency output of the sensor data to a specific frequency range. The modified data is then sent to a comparator with manually preset reference levels. The manually preset reference levels are utilized to identify the start of vocalization (when the sensor data exceeds a reference level) and to identify pathological voice problems, in order to send a feedback signal, when the sensor data drops below another reference level. By relying on a single sensor type and preset thresholds, these devices may trigger a feedback response for certain non-vocal inputs and may be unable to adjust for calibration issues commonly associated with the use of a particular sensor (e.g., accelerometer drift).

Prior art devices initiate audible feedback that is an audible alert adjusted for the ambient acoustic noise by a set dB value to induce a Lombard effect response on the patient. This may prove inadequate for treating patient's suffering from partial hearing loss as response to the Lombard effect would be reduced.

Other relevant background art is as follows:

a. Hess, W. 1983. Pitch Determination of Speech Signals, Springer Series of information Sciences, vol. 3, Springer-Verlag, Berlin, Heidelberg, New York (1983)
b. Ishi, C. T., Ishiguro, H., Hagita, N. 2005. Proposal of acoustic measures for automatic detection of vocal fry. In: Proceedings of Interspeech 2005, Lisbon, Portugal, pp. 481-484.
c. Schädler, M. R., Meyer, B. T. and Kollmeier, B., 2012. Spectro-temporal modulation subspace-spanning filter bank features for robust automatic speech recognition. The Journal of the Acoustical Society of America, 131(5), pp. 4134-4151.
d. Young, V. and Mihailidis, A., 2010. Difficulties in automatic speech recognition of dysarthric speakers and implications for speech-based applications used by the elderly: A literature review. Assistive Technology, 22(2), pp. 99-112.
e. Van Doremalen, J., Cucchiarini, C. and Strik, H., 2009. Optimizing automatic speech recognition for low-proficient non-native speakers. EURASIP Journal on Audio, Speech, and Music Processing, 2010(1), p. 1.
f. Junqua, J. C. and Haton, J. P., 2012. Robustness in automatic speech recognition: Fundamentals and applications (Vol. 341). Springer Science & Business Media.
g. Sharma, P. and Rajpoot, A. K., 2013. Automatic identification of silence, unvoiced and voiced chunks in speech. Journal of Computer Science & Information Technology (CS & IT), 3(5), pp. 87-96.

BRIEF SUMMARY

Disclosed herein are embodiments of a wearable vocal dosimeter giving real-time biofeedback and collecting long-term vocal data from users. In one embodiment, a first set of sensor data is received as sensor outputs from a plurality of sensors including an acoustic sensor, a piezoelectric sensor, and an accelerometer. An analog to digital converter converts the sensor outputs from the acoustic sensor, the piezoelectric sensor, and the accelerometer into raw acoustic wave, normalized acoustic wave, raw electrical wave, and normalized electrical wave. Laryngeal activity is detected and a user feedback device is activated to assist the user with adjusting their vocal characteristics.

The analog to digital converter may be operated to generate a feedback modification dataset including the normalized acoustic wave, the raw acoustic wave, the normalized electrical wave, and the raw electrical wave. A feedback response filter is operated on the feedback modification dataset to generate a behavior modification dataset that omits a feedback device activation signature from the normalized acoustic wave and which also omits the normalized electrical wave from the feedback modification dataset. The behavior modification dataset may be stored with association to the vocalization dataset in the vocal characteristic database.

In one embodiment, the modulator may be utilized to adjust the amplitude of the raw acoustic wave and to adjust the amplitude of the raw electrical wave during a period ranging between 100-2000 milliseconds, for an acoustic range between 25 dB SPL and 50 dB SPL. This produces the normalized acoustic wave for the acoustic sensor and the normalized electrical wave for the piezoelectric sensor and the accelerometer. A vocalization dataset including the normalized acoustic wave, the raw acoustic wave, the normalized electrical wave, and the raw electrical wave may be transmitted to the laryngeal activity detector.

The normalized acoustic wave and the normalized electrical wave for the piezoelectric sensor and the accelerometer from the vocalization dataset may be processed to generate articulatory data as controlled by a laryngeal activity detection algorithm. The articulatory data may be processed through an interpreter to determine vocal activity and to generate a feedback control as controlled by the laryngeal activity detector. The vocalization dataset and the articulatory data may be stored in a vocal characteristic database.

Stored articulatory characteristics associated with a stored feedback controls may be retrieved from the vocal characteristic database. The articulatory data may be matched to stored articulatory characteristics to identify similar articulatory characteristics within the stored articulatory characteristics, and to retrieve the stored feedback controls associated with the similar articulatory characteristics.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
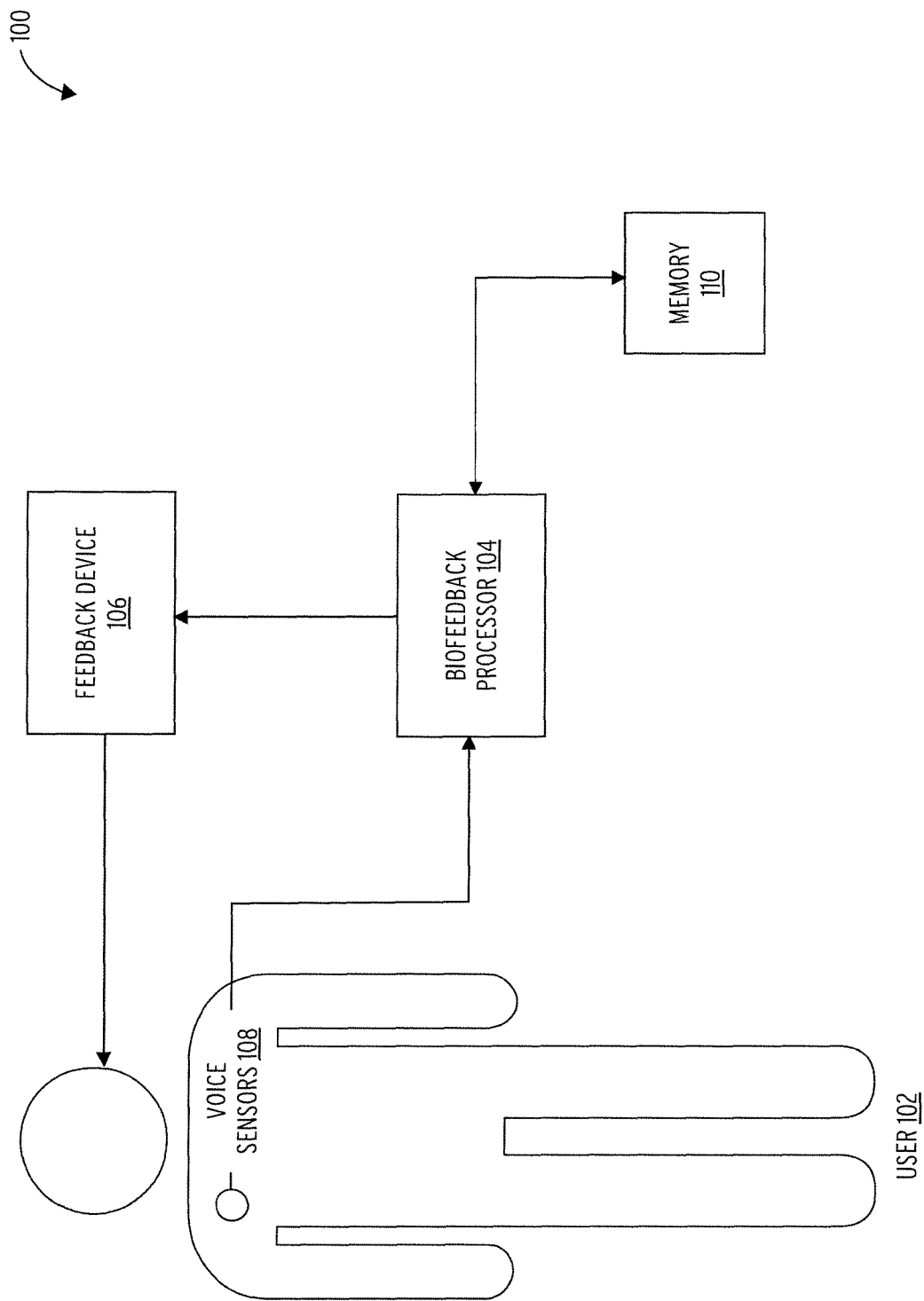
FIG. 1 illustrates a system environment 100 for operating a vocal dosimeter.

Disclosed herein are embodiments of a small, wearable device that records and processes speech and vocal features known to be important in the identification, treatment, and evaluation of persons with disordered speech. The device collects speech data for offline processing and evaluation, and provides real-time biofeedback to the user. The wearable device analyzes the speech data and provides the individual with real-time biofeedback information on vocal patterns to allow the wearer to adjust their speech and voice production.

The wearable device provides real time assistance by alerting the wearer to correct their speech or vocal pattern. This device is more effective management than costly face-to-face therapy with a speech-language pathologist which many people cannot afford. Using this wearable device improves the quality of life by allowing the user to maintain communication with less restriction and promotes a healthier lifestyle.

The device utilizes sensors (e.g., accelerometer, piezoelectric, acoustic, etc.) worn on or near the neck or collar bone of the user. The sensors detect vocal vibrations at a suitable sample rate for vocal and speech analysis. A processor and data storage accumulator (processing system) are coupled to the sensors—in one implementation, these components are approximately 3×5×8 cm and about 70 grams. The processing system may be implemented using a single-board computer with system-on-a-chip technology, a 700 MHz ARM processor, 512 MB RAM, and 32 GB fixed memory in a small casing with a battery. The processing system may further include a vibrator device, LED lights, and an integral acoustic speaker. The processing system may utilize an open-source Linux OS and may fit in the palm of the user's hand. The data from the accumulator may be encrypted to onboard flash memory (e.g., 32 GB). This may provide up to 400 continuous hours of run-time capacity, subject to memory and battery limitations. Additional modifications may add add wireless capabilities, additional sensor channels, and network capabilities, for example.

The sensors on the neck or collarbone may be connected by electrical leads to the accumulator. A mounted vibrator device may generate biofeedback. Signals from the sensors are converted from analog to digital to give real-time feedback to haptic, visual, and/or auditory devices and to log sensor activity for offline analysis. A first set of sensor data may be analyzed to determine if there is live human vocal activity and to thus activate the additional analysis and feedback processes.

The signal-to-noise ratio of estimated vocal or laryngeal activity may utilize a pitch determination algorithm to detect the fundamental frequency and the microphone's acoustic noise signal. The system limits resource allocation and processing to preserve memory and battery life if no fundamental frequency detected. If live human vocal activity is detected, laryngeal activity and acoustic signal are collected and evaluated and streamed to the memory of the recording device. These signals are evaluated in real-time and if vocal amplitude does not meet the predetermined amplitude threshold(s), feedback is generated to the user via the haptic, visual, or auditory transducers. Feedback may stop when the amplitude exceeds a lower threshold, such as the 50 dB threshold of the feedback activation range.

This system may be enhanced with wireless data streaming, additional sensor channel inputs, and/or feedback threshold adjustments with networking capability. Software and control settings may be configured, updated, or activated remotely.

Thus, in a first processing stage, the first set of sensor data is evaluated to determine the presence of live human vocal activity of the wearer. This may be accomplished using the signal-to-noise ratio of estimated vocal or laryngeal activity (including the presence of fundamental frequency via a pitch determination algorithm) and the ambient acoustic noise signal from the microphone. If no vocal activity is detected, the device limits system resources to preserve memory and battery life. If live human vocal activity is detected, the second processing stage is initiated in which laryngeal activity and the acoustic signal are collected from the sensors, evaluated in real time, and streamed to the memory of the processing device. The signal is evaluated in real-time to determine if user feedback is to be generated. If vocal amplitude does not meet configured amplitude thresholds, feedback to the user is initiated via the haptic, visual, or auditory transducers of the system.

The memory may store natural audio sampled and stored in a high-quality, lossless format (such as 22.05 kHz, 16-bit, pulse-code modulated, or WAV format), including additional classification variables such as demographic, age, disease progression, and speaker gender. The recorded first set of sensor data is compared with vocal characteristics of the stored audio samples and to determine presence of (vocal) pathology. Vocal characteristics include vocal amplitude, fundamental frequency, voicing, windowed and absolute syllable/sonorant-peak rate, signal-to-noise ratio, and temporal and spectral characteristics. Sampled data is compared with stored data for statistical likelihood to categorize the sampled data as pathological or non-pathological. The memory includes vocal samples from speakers with disorders in both normal and pathological conditions, and from speakers without disorders. Samples from users are further stored to provide data inputs to the likelihood algorithms that determine presence of vocal pathology.

The vocal dosimeter may utilize a sensor array that includes an accelerometer, a piezoelectric, and acoustic sensors. The piezoelectric sensor measure changes in pressure, acceleration, temperature, strain, or force by converting them to an electrical charge. The accelerometer detects the magnitude and direction of proper acceleration as a vector quantity. Thus in order to effectively detect vocalization, the piezoelectric sensor and the accelerometer are positioned coincident or proximal to resonant cavities of the body such as the bony structures of the clavicle or the thyroid/cricoid cartilage near vocal folds in order to detect the movement or pressure changes associated vocalization.

The acoustic sensor may be accomplished by a microphone. While the piezoelectric sensor and the accelerometer require adjacent or proximal positioning to resonant cavities, the acoustic sensor may depend on the microphone or preference of the user. In order to account for unwanted variations, the sensors may undergo a calibration process to reduce processing issues.

In order to reduce false negatives and false positive conditions (as well as the "hit" and "correct rejection" rates) the laryngeal activity detection logic and the feedback logic may utilize a confusion matrix. Additionally, other techniques may be utilized, such as Bayesian residuals, to estimate error or imprecision. By accumulating the raw data and normalized data, error estimate may be generated to adjust the algorithm to reduce errors and/or quantify the error to build it into a processing model.

Vocalization is always bounded by silence, or very-low amplitude, aperiodic noise (not determined to be energy emanating from the excitation of the human vocal tract). In practice, this is very obvious because the sensors are attached the resonant cavities (i.e., the body of the talker), thus the thresholds maybe set to <5% of RMS amplitude over some large window (maybe 100 000 ms, or even the whole recording).

During the ADC stage, an amplitude for each sensor may be generated and then normalized relative to the feedback activation range (25 dB-50 dB) during a sampling window between 100-2000 milliseconds. The normalization is done on a vector of numbers.

The laryngeal activity detector laryngeal activity is determined continuously, typically in a 2-5 ms sliding window. That analysis frame (2-5 ms) determines the likelihood of that segment being "on" or "off" for laryngeal activity; then it slides to the right by 1 ms (which overlaps with the previous segment) and repeats. The likelihood measures are then tallied and some threshold for whether that's voiced or not (that is, "laryngeal activity or not") is determined. The parameters are to a large degree empirically determined. the parameters, changing the moving window to slide, say 2 ms rather than 3, and let the system "emerge" or "settle into an attractor state" by empirical means.

The amplitude is the observed values from the sensor. The sensor gives both negative and positive values and is not normalized. To account for these two facts, the values are squared and then the square root is computed (to essentially get rid of the negative and positive values and obtain an absolute value of sorts) and then the data are normalized to fit into an interpretable range.

A vocal dosimeter may include a plurality of sensors, an analog to digital converter, a laryngeal activity detector, a set of raw wave data and normalized wave data, and a user feedback device. The plurality of sensors comprises an acoustic sensor, a piezoelectric sensor, and an accelerometer. The analog to digital converter comprises a sensor transducer and a modulator. The sensor transducer receives raw data from the plurality of sensors. The analog to digital converter generates a set of raw wave data and normalized wave data comprising raw acoustic wave and normalized acoustic wave processed from the acoustic sensor, and raw electrical wave and normalized electrical wave processed from the piezoelectric sensor and the accelerometer. The laryngeal activity detector operates a processor, a feedback controller, and an interpreter. The processor receives the set of raw wave data and normalized wave data and processes it to generate articulatory data using a laryngeal activity detection algorithm. The interpreter generates a feedback control. The feedback controller is controlled by the feedback control. The database receives and stores vocalization dataset, articulatory data, feedback control, and feedback modification dataset. The database communicates stored articulatory characteristics and a stored feedback controls to the interpreter.

A method of operating a vocal dosimeter receives a first set of sensor data as sensor outputs from a plurality of sensors comprises an acoustic sensor, a piezoelectric sensor, and an accelerometer at a sensor transducer. The analog to digital converter is operated to convert the sensor outputs from the acoustic sensor, the piezoelectric sensors, and the accelerometer into a vocalization dataset including normalized acoustic wave and raw acoustic wave from the acoustic sensor and normalized electrical wave and raw electrical wave from the piezoelectric sensor and the accelerometer. The method of operating a vocal dosimeter operates the laryngeal activity detector in. The laryngeal activity detector processes the normalized acoustic wave and the normalized electrical waves from piezoelectric sensor and the accelerometer from the vocalization dataset and generates articulatory data as controlled by a laryngeal activity detection algorithm. The laryngeal activity detector operates an interpreter processes articulatory data to determine vocal activity and a feedback control. The laryngeal activity detector communicates the vocalization dataset and the articulatory data to the vocal characteristic database and communicates the feedback control to a feedback controller. The feedback controller activates a user feedback device as controlled by the feedback control. The sensor transducer receives a second set of sensor data following activation of the user feedback device. The analog to digital converter is operated to generate a feedback modification dataset comprising the normalized acoustic wave and the raw acoustic wave from the acoustic sensor and the normalized electrical wave and the raw electrical wave from the piezoelectric sensor and the accelerometer. The feedback response filter is operated to generate a behavior modification dataset by omitting a feedback device activation signature from the normalized acoustic wave and the normalized electrical wave from the feedback modification dataset. The behavior modification dataset is associated with the vocalization dataset and stored in the vocal characteristic database.

The vocal dosimeter receives a second set of sensor data at the sensor following activation of the user feedback device and in response operates the analog to digital converter to generate a feedback modification dataset that includes the normalized acoustic wave, the raw acoustic wave, the normalized electrical wave, and the raw electrical wave. A feedback response filter is utilized to generate a behavior modification dataset by omitting a feedback device activation signature from the normalized acoustic wave and the normalized electrical wave from the feedback modification dataset. The behavior modification dataset may then be stored and associated to the vocalization dataset in the vocal characteristic database.

The operation of the analog to digital converter may include controlling a transducer to convert the sensor outputs from the acoustic sensor, the piezoelectric sensor and the accelerometer into a raw acoustic wave, for the acoustic sensor, and the raw electrical wave for the piezoelectric sensor and the accelerometer. The analog to digital convert may control the modulator to adjust an amplitude of the raw acoustic wave and the amplitude of the raw electrical wave during a period ranging between 100-2000 milliseconds to correspond to an acoustic range between 25 dB SPL and 50 dB SPL, thus producing the normalized acoustic wave and the normalized electrical wave. The analog to digital convert may transmit the normalized acoustic wave, the raw acoustic wave, the normalized electrical wave, and the raw electrical wave as a vocalization dataset to the laryngeal activity detector.

The processing of the articulatory data through the interpreter to determine the vocal activity and the feedback control as controlled by the laryngeal activity detector may include communicating with the vocal characteristic database to retrieve stored articulatory characteristics associated with a stored feedback control. The articulatory data may be matched to the stored articulatory characteristics to identify similar articulatory characteristics within the stored articulatory characteristics. Upon identifying a matched the stored feedback controls associated with the similar articulatory characteristics are retrieved.

Referencing FIG. 1, a system environment 100 for operating a vocal dosimeter comprises a user 102, with a voice sensors 108 attached to the user 102. A biofeedback processor 104 is connected to the voice sensors 108. The biofeedback processor 104 is communicably coupled to a memory 110. The biofeedback processor 104 controls a feedback device 106.

Figure 2:
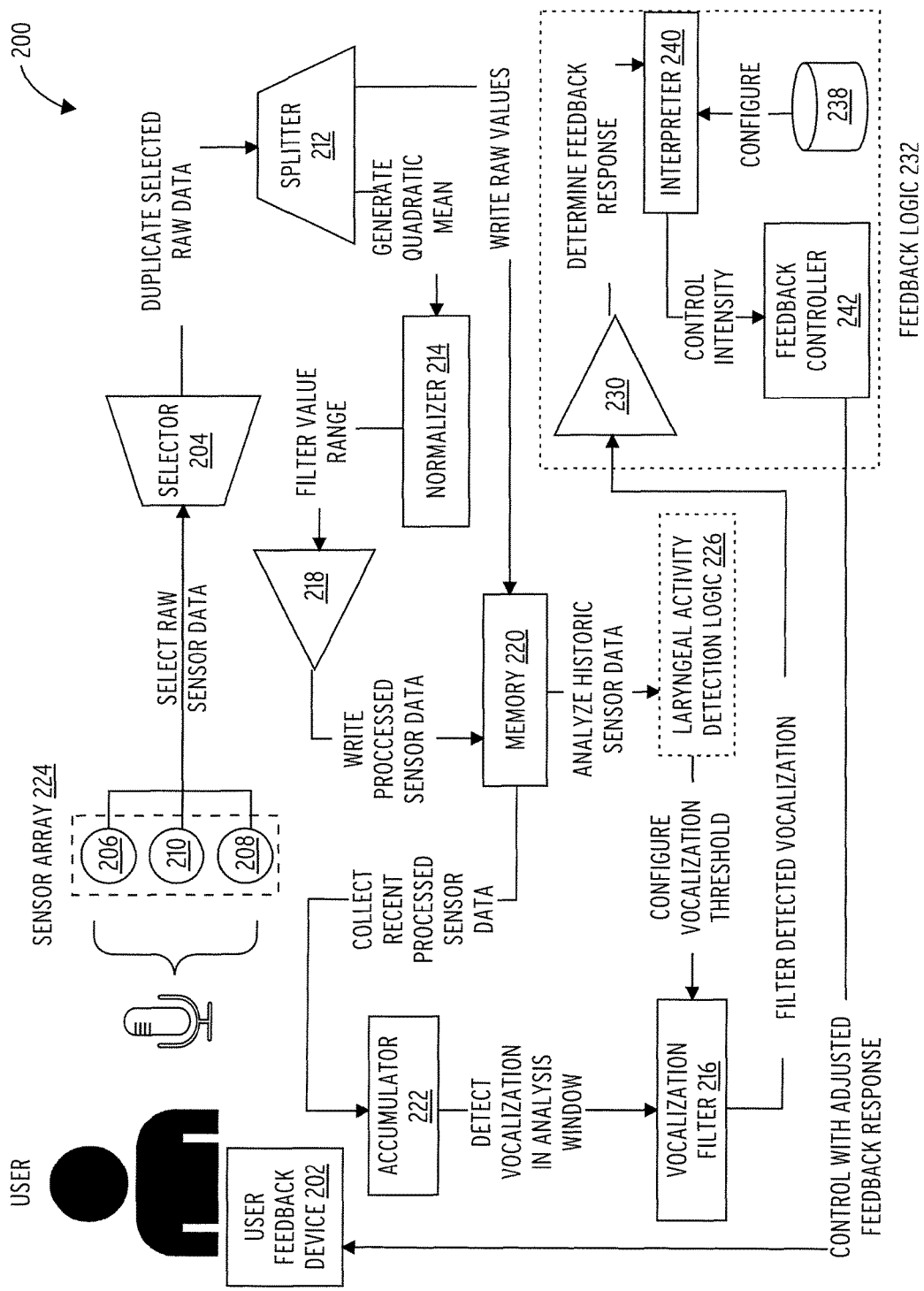
FIG. 2 illustrates an embodiment of a vocal dosimeter 200.

Referencing FIG. 2, a vocal dosimeter 200 comprises a sensor array 224, a selector 204, a splitter 212, a normalizer 214, a first band-pass filter 218, a controlled memory data structure 220, an accumulator 222, a vocalization filter 216, laryngeal activity detection logic 226, feedback logic 232, and a user feedback device 202. The sensor array 224 comprises an acoustic sensor 206, a piezoelectric sensor 210, and an accelerometer 208. The feedback logic 232 comprises a second band-pass filter 230, an interpreter 240, a vocalization characteristic database 238, and a feedback controller 242.

The sensor array 224 generates sensor outputs from user vocalization. The selector 204 selects raw sensor data from each sensor of the sensor array. The splitter 212 duplicates the raw sensor data for storage in the controlled memory data structure 220 and to send to the normalizer 214. The normalizer 214 generates a quadratic mean (root mean square) for each raw sensor data. The first band-pass filter 218 takes the normalized sensor data from each sensor and filters for a value range to generate processed sensor data. The processed sensor data is stored within the controlled memory data structure 220. The accumulator 222 collects recently processed sensor data stored in the controlled memory data structure 220 and generates a combined sensor amplitude. The laryngeal activity detection logic 226 analyzes historic sensor data and configures the vocalization filter 216 with the vocalization threshold. The second band-pass filter 230 filters the combined sensor amplitude for feedback activity. The interpreter 240 determines a feedback response in the form of a feedback control from the feedback activity. The vocalization characteristic database 238 configures the interpreter 240. The feedback controller 242 receives the feedback control and adjusts the feedback generated by the user feedback device 202.

The vocal dosimeter 200 may be operated in accordance with the processes described in the FIGS. 3-9.

Figure 3:
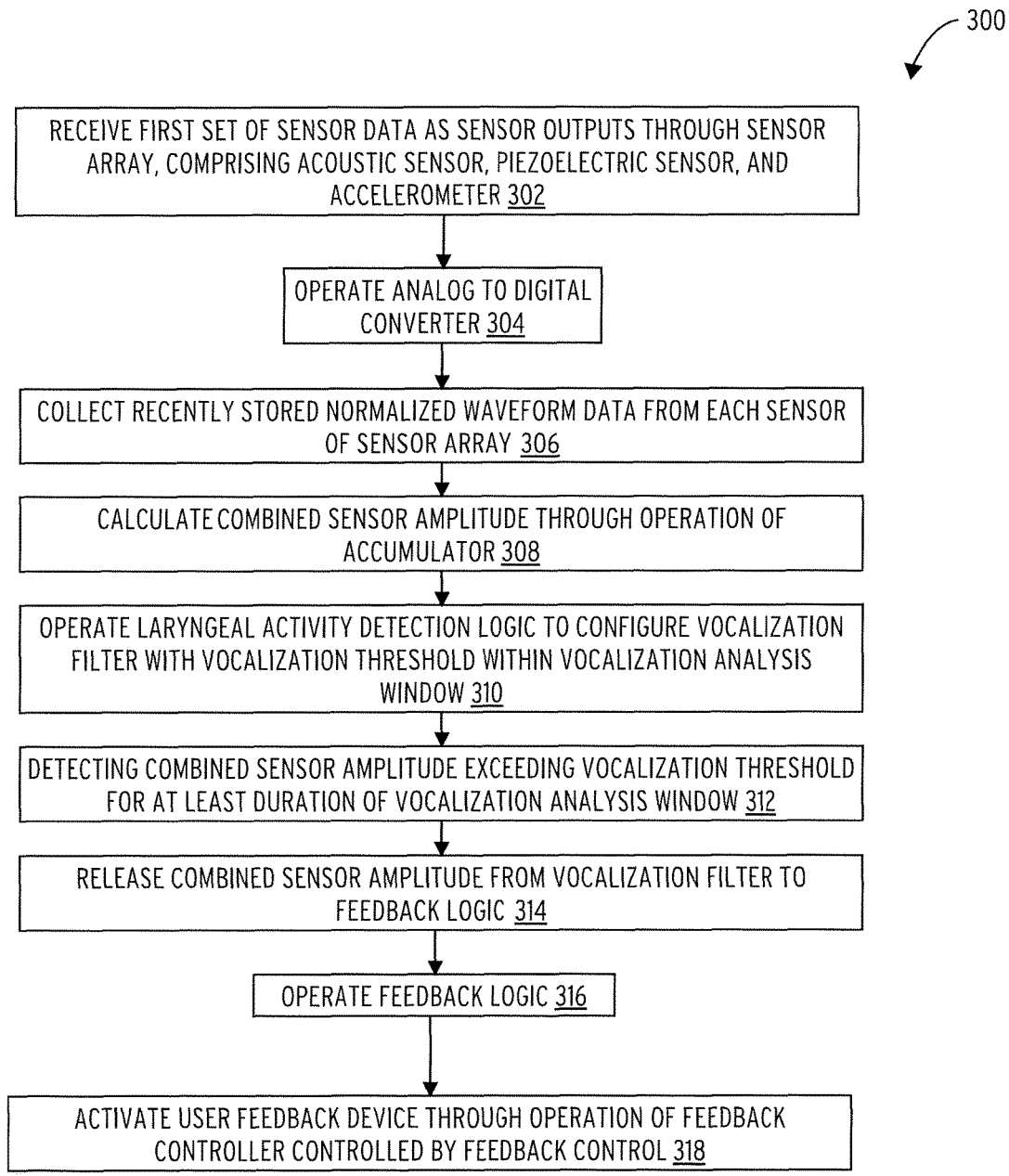
FIG. 3 illustrates an embodiment of a method of operating a vocal dosimeter 300.

Referencing FIG. 3, a method of operating a vocal dosimeter 300 receives a first set of sensor data as sensor outputs through an acoustic sensor, a piezoelectric sensor, and an accelerometer of a sensor array (block 302). The method of operating a vocal dosimeter 300 operates an analog to digital converter (block 304). The accumulator collects recently stored normalized waveform data from each sensor of the sensor array (block 306). The accumulator calculates the combined sensor amplitude from the recently stored normalized waveform data (block 308). The laryngeal activity detection logic configures the vocalization filter to detect a vocalization threshold occurring within vocalization analysis window (block 310). The vocalization filter detects the combined sensor amplitude exceeding the vocalization threshold for at least the duration of the vocalization analysis window (block 312). The vocalization filter releases the combined sensor amplitude to the feedback logic (block 314). The method of operating a vocal dosimeter 300 operates the feedback logic (block 316). The feedback controller activates the user feedback device as controlled by a feedback control (block 318).

One embodiment of an algorithm to determine amplitude threshold and provide feedback is as follows:

1. Sample the first set of sensor data directly, putting raw values into working memory.

2. Compute the raw values of each sensor in terms of amplitude, normalized to the acoustic threshold corresponding to not less than 25 dB SPL and not more than 50 dB SPL. The sampling analysis window is set to 100-2000 milliseconds (or about the minimum and maximum duration of a syllable) with relative mean speech production amplitude imputed over the duration of the window. The computed raw values are then input to the laryngeal activity stage.

3. The laryngeal activity stage determines speech voicing from short-time spectra obtained from the acoustic microphone and power measurements from the accelerometer and piezoelectric sensors, respectively. The non-zero input signal in this frame, s, is processed (e.g., in its entirety) to obtain the normalized result, μi.

$$\mu i = \Sigma_{j=m}^{[\omega,\varphi,\rho]} s j \qquad \text{Equation 1.1}$$

4. When μi is interpreted to correspond to the window 25-50 dB SPL, feedback to the user is initiated.

5. The raw and processed values are recorded to memory.

6. Feedback is recorded to memory and evaluated in a further processing stage to assess the result of intended behavior modification. Feedback, f, is assumed to be a linear inverse finite sequence of initiated feedback to the user, given in 1.2 below.

$$M=f'(y)=f(f^{-1}(x))$$  Equation 1.2

7. Raw and processed data is stored in nonvolitile memory and communicated to a database for further analysis and algorithm refinement.

Figure 4:
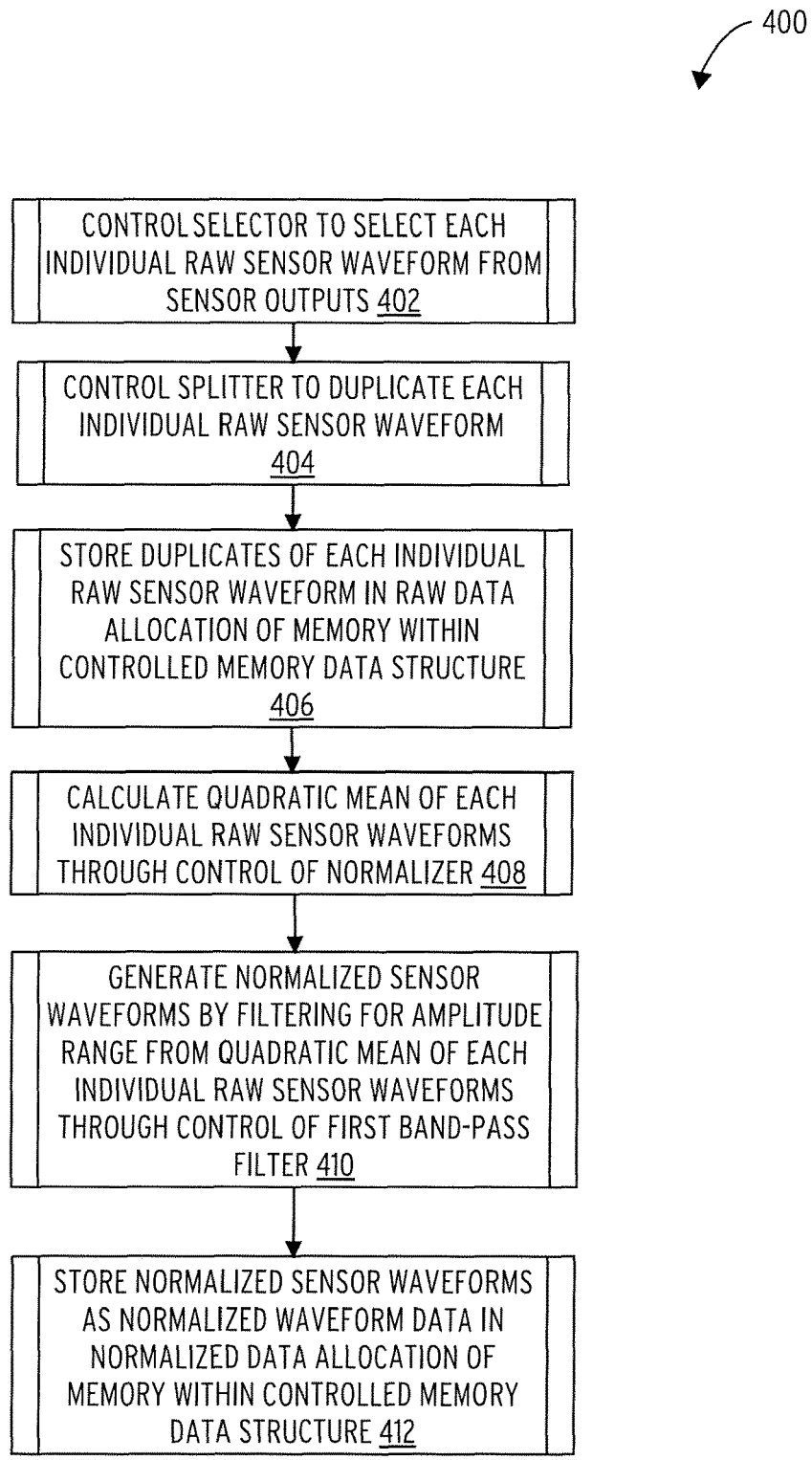
FIG. 4 illustrates an embodiment of a process of operating an analog to digital converter 400.

Referencing FIG. 4, the process of operating an analog to digital converter 400 controls the selector to select for each individual raw sensor waveform from the sensor outputs (subroutine block 402). The analog to digital converter controls the splitter to duplicate each of the individual raw sensor waveform (subroutine block 404). The analog to digital converter stores duplicate of each individual raw sensor waveform in the raw data allocation of memory within the controlled memory data structure (subroutine block 406). The analog to digital converter controls the normalizer to calculate the quadratic mean for each of the individual raw sensor waveforms (subroutine block 408). The analog to digital converter controls the band-pass filter to generate normalized sensor waveforms by filtering for an amplitude range in the quadratic mean of each of the individual raw sensor waveforms (subroutine block 410). The analog to digital converter stores the normalized sensor waveforms as normalized waveform data in a normalized data allocation of memory within the controlled memory data structure (subroutine block 412).

Figure 5:
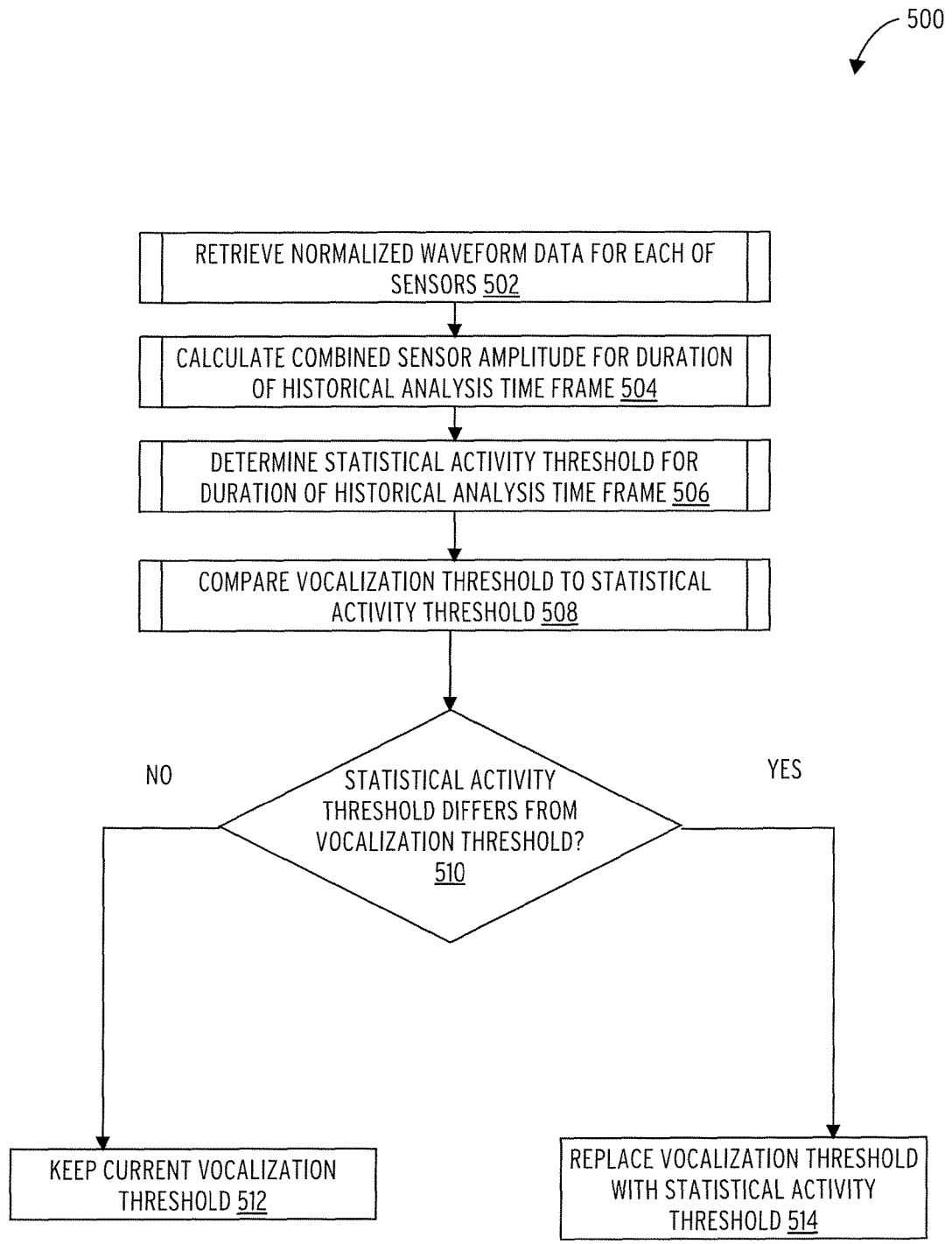
FIG. 5 illustrates an embodiment of the process 500 of operating laryngeal activity detection logic.

Referencing FIG. 5, a process 500 of operating laryngeal activity detection logic retrieves the normalized waveform data for each of the sensors in the controlled memory data structure (subroutine block 502). The laryngeal activity detection logic calculates the combined sensor amplitude for duration of historical analysis time frame (subroutine block 504). The laryngeal activity detection logic determines the statistical activity threshold for duration of historical analysis time frame (subroutine block 506). The laryngeal activity detection logic compares the vocalization threshold to statistical activity threshold (subroutine block 508). The laryngeal activity detection logic tests the difference between the statistical activity threshold and the vocalization threshold (decision block 510). If the statistical activity threshold differs from the vocalization threshold, the vocalization threshold is replaced with the statistical activity threshold (block 514). If the statistical activity threshold does not differ from the vocalization threshold, the current vocalization threshold is kept (block 512).

Figure 6:
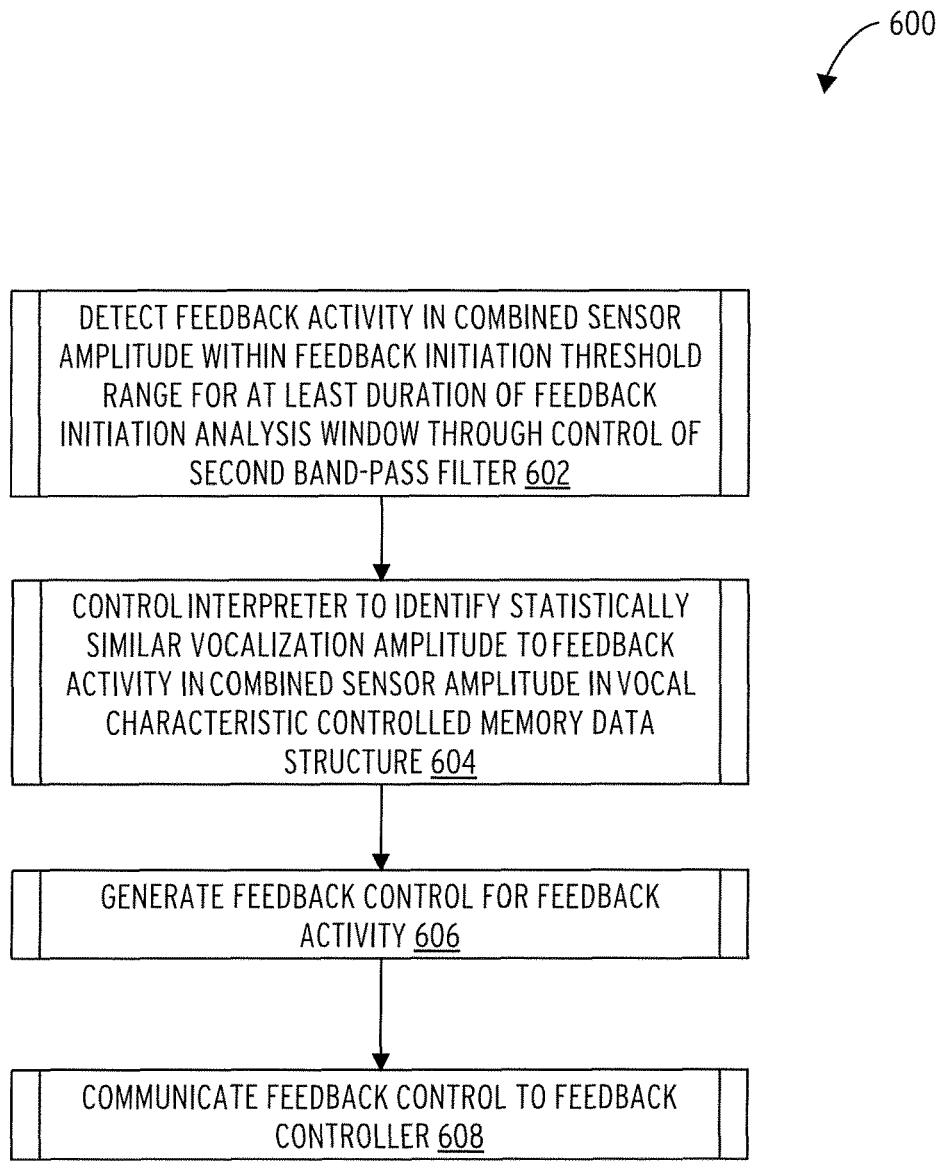
FIG. 6 illustrates an embodiment of a process 600 of operating feedback logic.

Referencing FIG. 6, a process 600 of operating feedback logic controls the second band-pass filter to detect feedback activity in the combined sensor amplitude within feedback initiation threshold range for at least the duration of feedback initiation analysis window (subroutine block 602). The feedback logic controls the interpreter to identify statistically similar vocalization amplitude to the feedback activity in the combined sensor amplitude in the vocal characteristic controlled memory data structure (subroutine block 604). The feedback logic generates a feedback control for the feedback activity (subroutine block 606). The feedback logic communicates the feedback control to the feedback controller (subroutine block 608).

Figure 7:
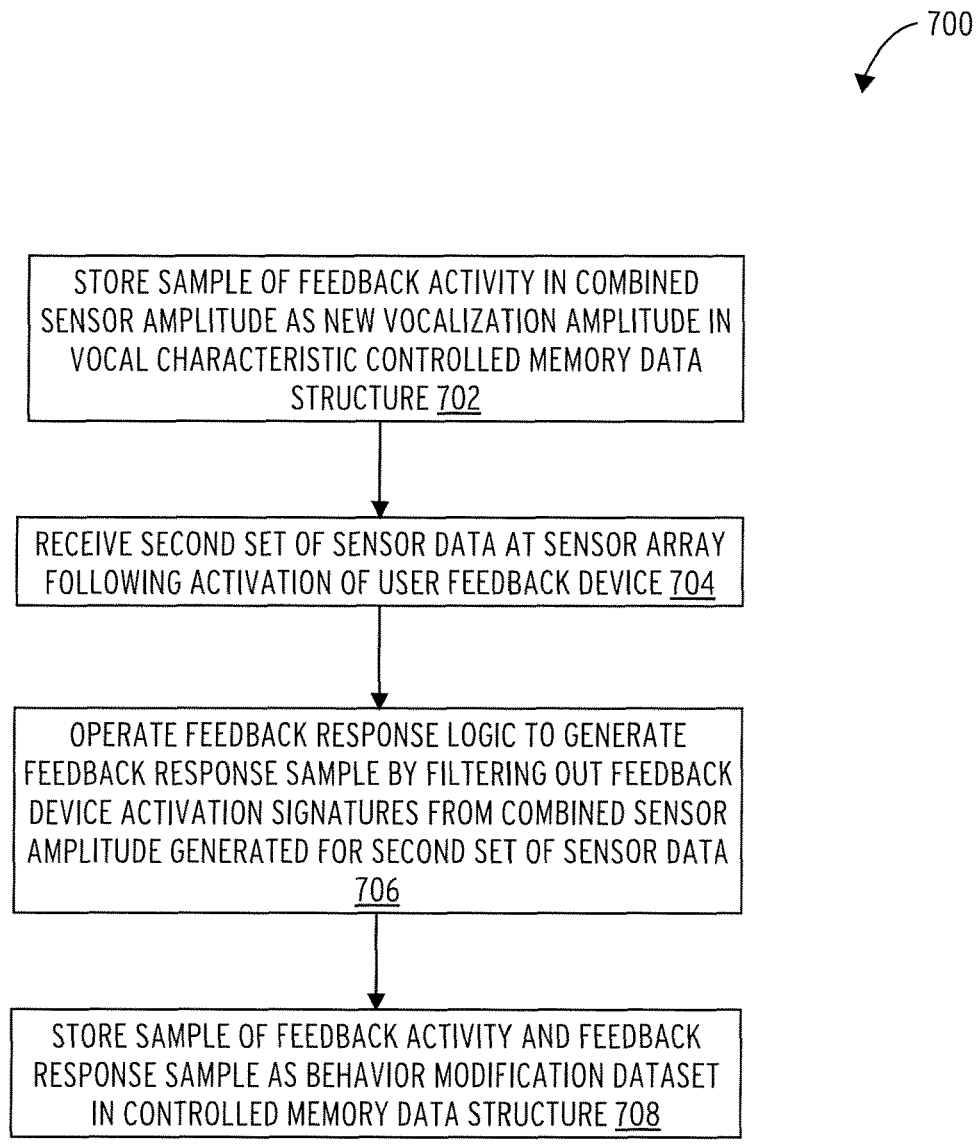
FIG. 7 illustrates an embodiment of a process 700 of operating vocal dosimeter.

Referencing FIG. 7, a process 700 of operating vocal dosimeter stores sample of the feedback activity in the combined sensor amplitude as a new vocalization amplitude in the vocal characteristic controlled memory data structure (block 702). The sensor array receives a second set of sensor data following activation of user feedback device (block 704). The feedback response logic generates a feedback response sample by filtering out feedback device activation signatures from the combined sensor amplitude generated from the second set of sensor data (block 706). The process 700 stores the sample of feedback activity and the feedback response sample as s behavior modification dataset in the controlled memory data structure (block 708).

Figure 8:
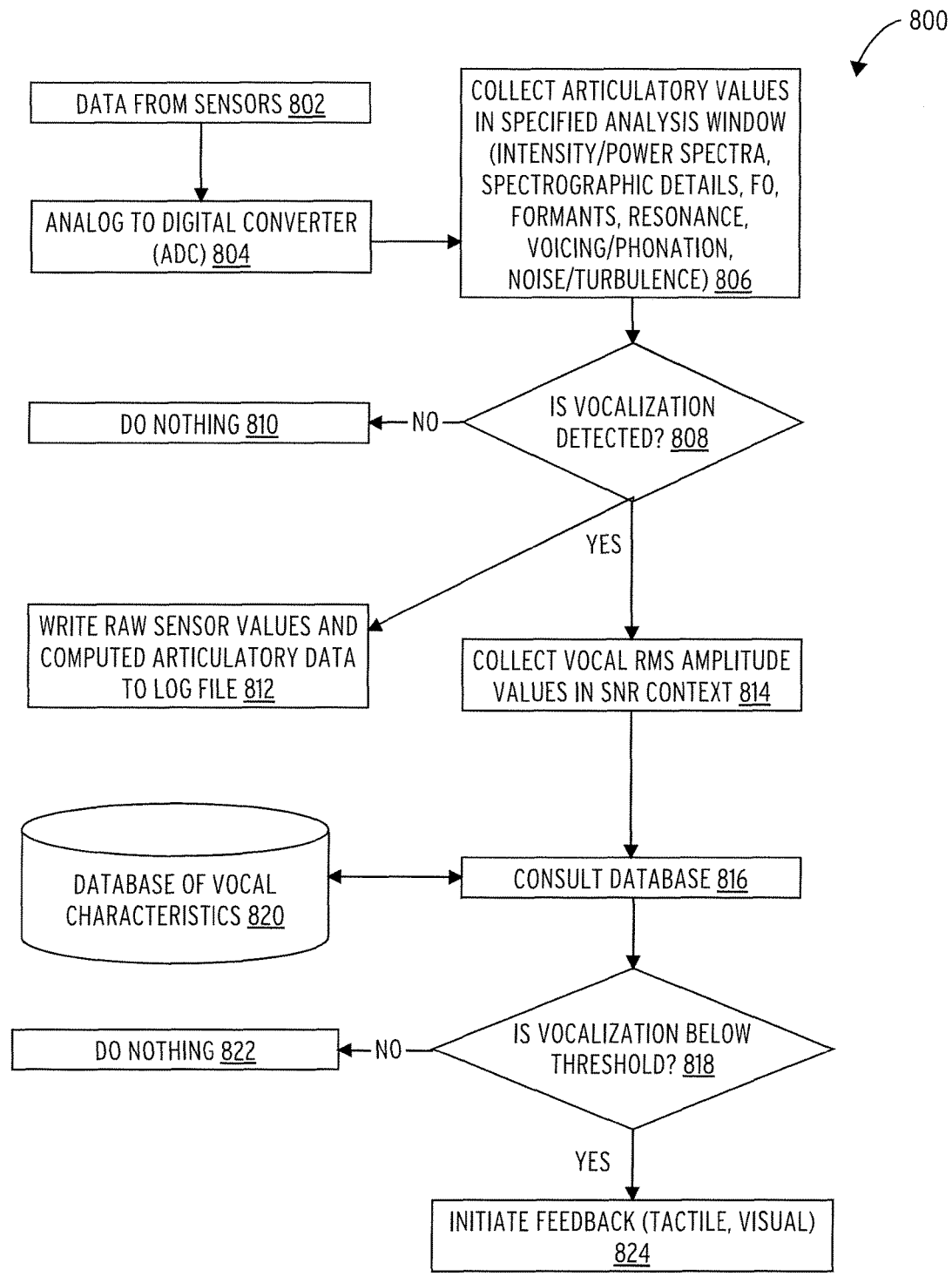
FIG. 8 illustrates an embodiment of a dosimeter activation process 800.

Referencing FIG. 8, the dosimeter activation process 800 receives raw data from the plurality of sensors block 802. The raw data is received and normalized by the analog to digital converter (block 804). The analog to digital converter transmits the data to the laryngeal activity detector to process the normalized data and collect articulatory values in a specified analysis window (intensity/power spectra, spectrographic details, formants, resonance, voicing/phonation, and noise/turbulence) (block 806).

The processed values are monitored for vocalization (decision block 808). If values are outside of the threshold window, nothing happens (block 810). If vocalization is detected in the processed values, the raw sensor values and the computed articulatory data are written to a log file (block 812) and the dosimeter activation process 800 collects the Root Mean Square (RMS) amplitude values and the signal to noise ratio (SNR) context (block 814).

The collected values for the RMS amplitude and the SNR context are used to consult a database of vocal characteristics 820 (block 816), after which a determination is made as to whether vocalization is below threshold (decision block 818). If the vocalization is below threshold, no action is taken (block 822). If the vocalization is above the threshold, the feedback is initiated (block 824).

Figure 9:
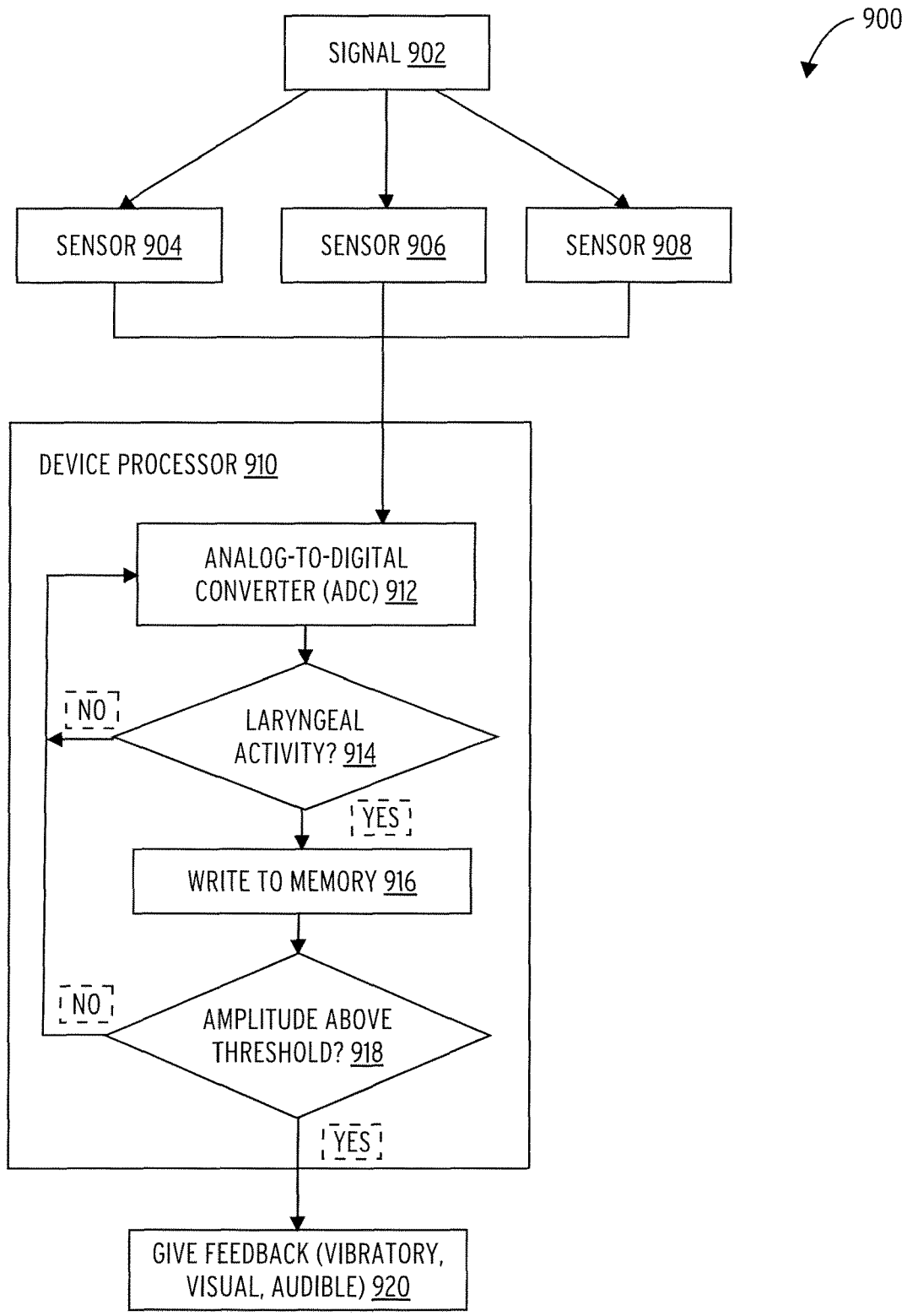
FIG. 9 illustrates an embodiment of a vocalization dosimeter 900 represented as a system diagram.

Referencing FIG. 9, a vocalization dosimeter 900 comprises an acoustic sensor 904, a piezoelectric sensor 906, an accelerometer 908, and a device processor 910. The acoustic sensor 904, the piezoelectric sensor 906, and the accelerometer 908 receive a signal 902 and transmit the data to the device processor 910. The device processor 910 receives the sensor data at an analog-to-digital converter (ADC) 912.

The analog-to-digital converter (ADC) 912 normalizes the data and transmits it to the processing stage. The processing stage analyzes the normalized data to determine the presence of laryngeal activity (decision block 914). If laryngeal activity is not detected, the device processor waits for more inputs from the analog-to-digital converter (ADC) 912. If laryngeal activity is detected, the normalized data and the raw data are written to memory 916.

The normalized data is then processed to determine whether the vocalization is above threshold (decision block 918). If the vocalization is below threshold, the device processor waits for more inputs from the analog-to-digital converter (ADC) 912. If vocalization is detected, a feedback device is activated to give feedback (vibratory, visual, audible) (block 920).

Figure 10:
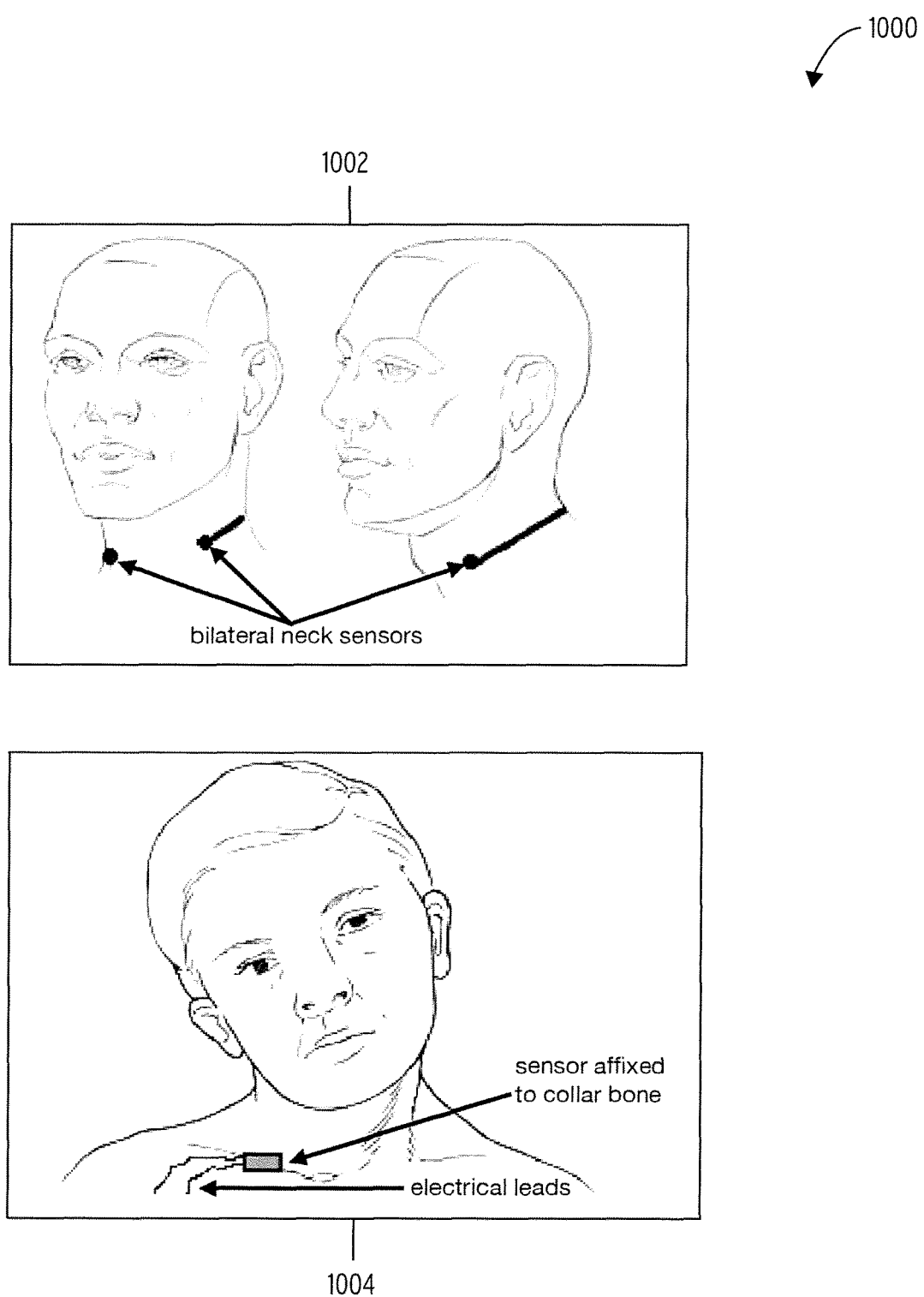
FIG. 10 illustrates an embodiment of sensor placement 1000.

Referencing FIG. 10, sensor placement 1000 illustrates the positioning of the plurality of sensors. The sensors may be placed in a bilateral configuration of a user's neck as illustrated in bilateral neck sensor placement 1002. Additionally the sensors may be affixed to a user's collar bone as illustrated in affixed to collar bone sensor placement 1004. In the affixed to collar bone sensor placement 1004 electrical leads can be seen coming out of the sensor.

Figure 11:
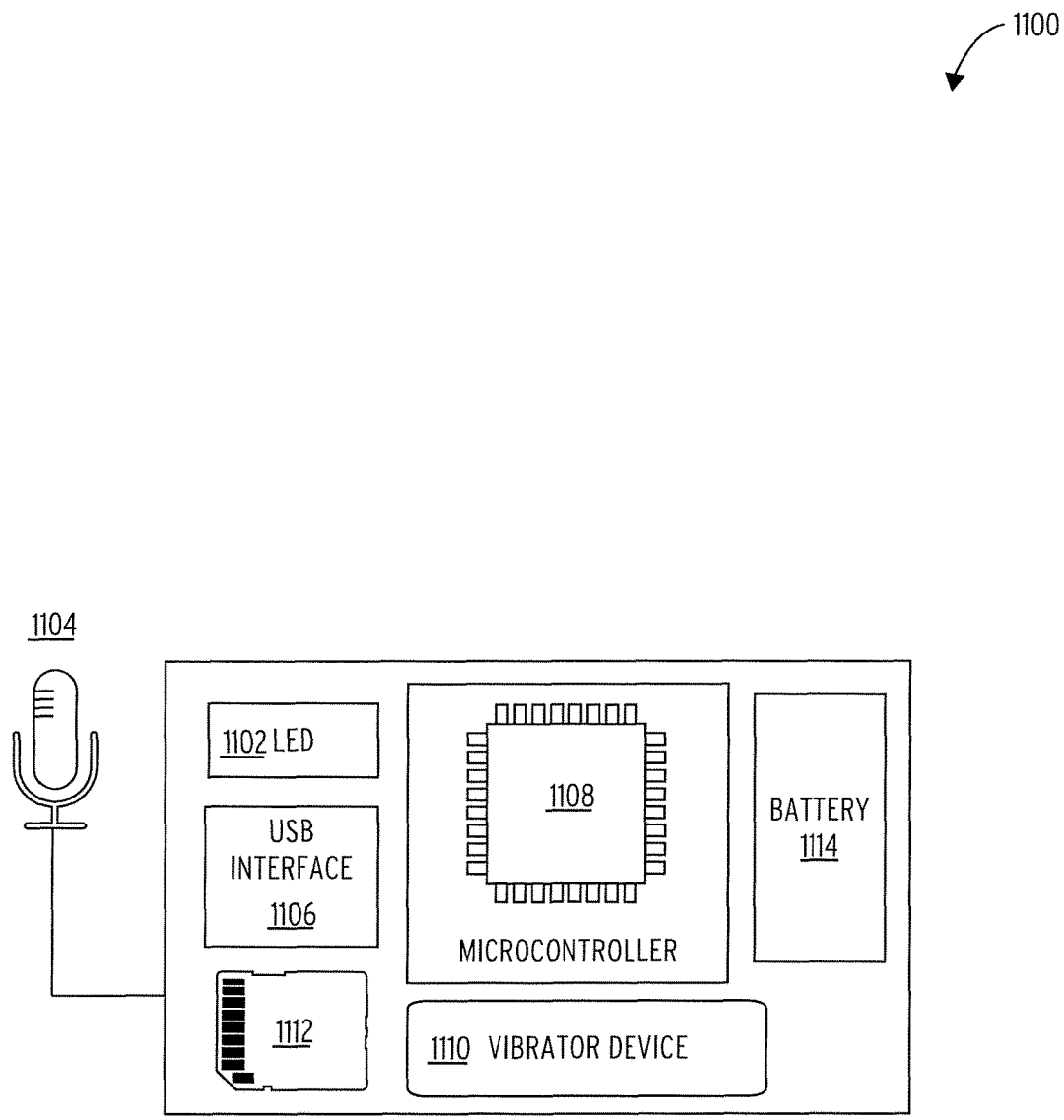
FIG. 11 illustrates an embodiment of a vocal dosimeter 1100.

Referencing FIG. 11, an embodiment of a vocal dosimeter 1100 may include a sensor 1104, an LED 1102, a USB interface 1106, a device storage 1112, a micro-controller 1108, vibrator device 1110, and a battery 1114.

The mounted vibrator device 1110 generates biofeedback from sensor data collected by the sensor 1104. The sensors may be mounted to a neckband or placed on clavicle or thyroid/cricoid cartilage near the vocal folds. The LED 1102 display is used for testing purposes. A battery 1114, such as a traditional 9-volt battery, may be utilized as the power source. The sensor data may be collected and stored in the device storage 1112. The USB interface 1106 may be utilized to configure the logic operating the micro-controller 1108. The vibrator device 1110 may be utilized to administer a vibratory feedback to a user.

Figure 12:
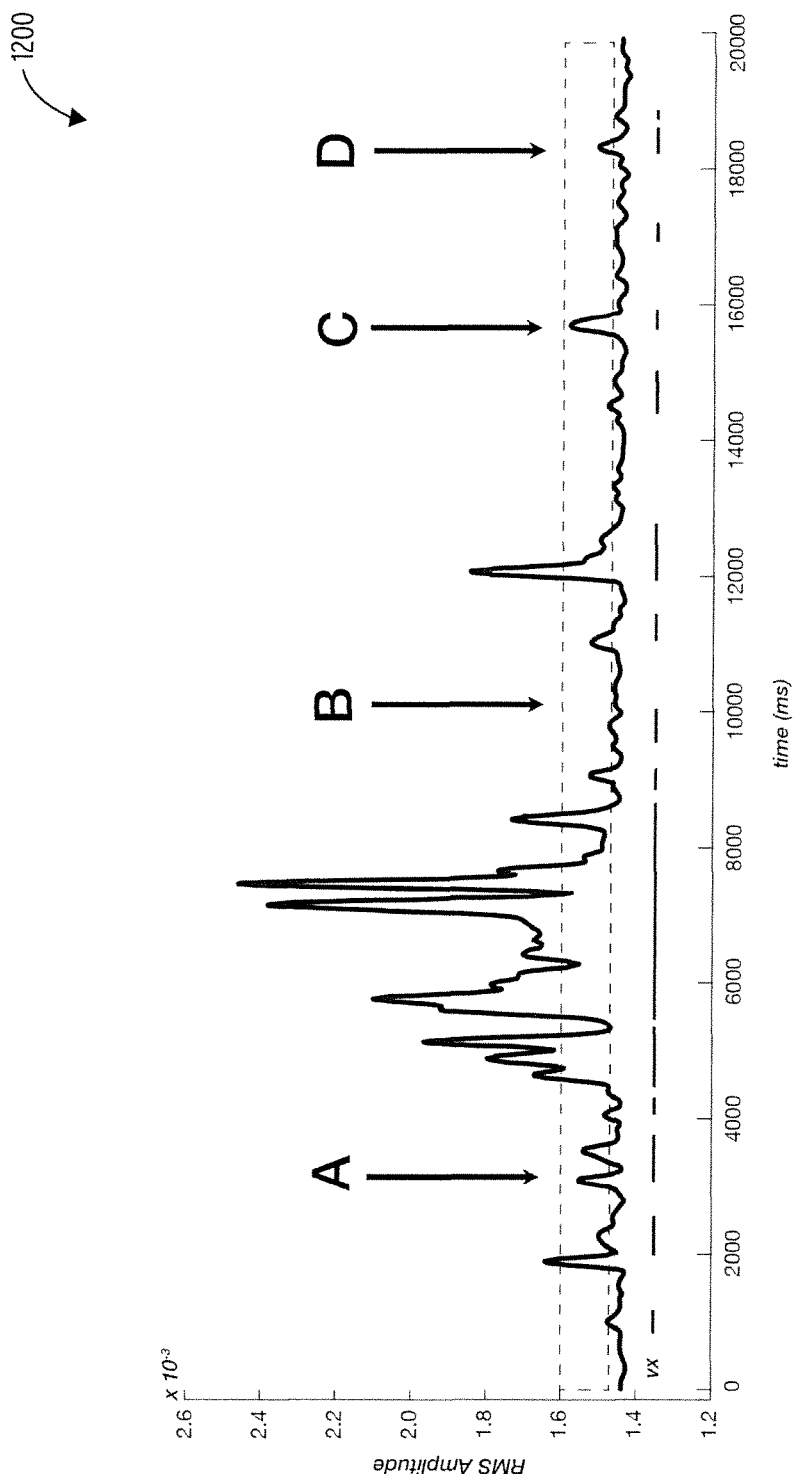
FIG. 12 illustrates a vocalization threshold window 1200.

Referencing FIG. 12, the vocalization threshold window 1200 can be seen with the processed sensor data normalized for the root mean square (RMS) amplitude. The vocalization threshold window 1200 shows that feedback is generated at point A as it is within the vocalization threshold (the signal is both voiced and within the threshold limit). Points B-D fail to meet the vocalizations thresholds. Point B falls below the threshold window, Point C is slightly above the threshold window, and Point D fails to meet the minimum duration to fit within the threshold window.

Figure 13:
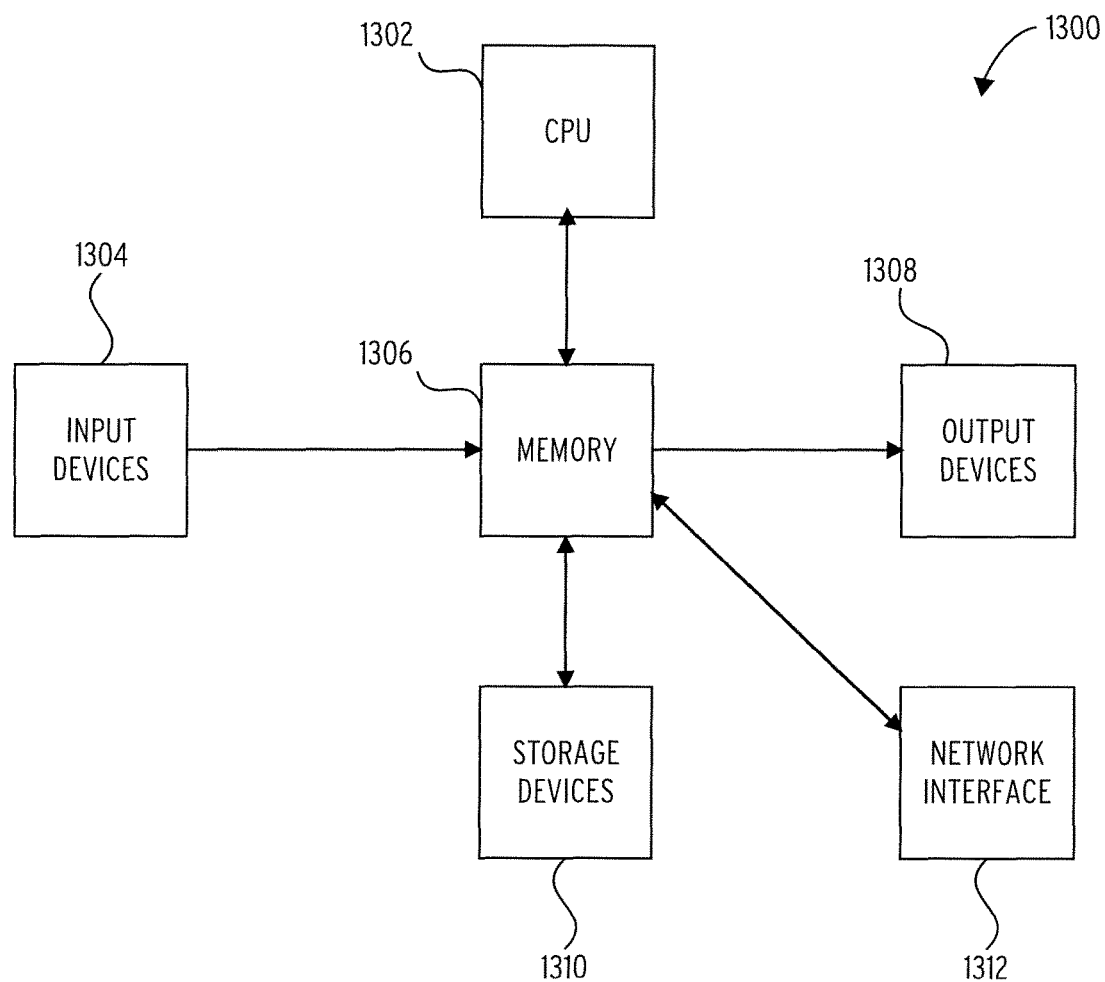
FIG. 13 illustrates an embodiment of a digital apparatus 1300 to implement components and process steps of the system described herein.

FIG. 13 illustrates an embodiment of a digital apparatus 1300 to implement components and process steps of the system described herein. Input devices 1304 comprise transducers that convert physical phenomenon into machine internal signals, typically electrical, optical or magnetic signals. Signals may also be wireless in the form of electromagnetic radiation in the radio frequency (RF) range but also potentially in the infrared or optical range. Examples of input devices 1304 are keyboards which respond to touch or physical pressure from an object or proximity of an object to a surface, mice which respond to motion through space or across a plane, microphones which convert vibrations in the medium (typically air) into device signals, scanners which convert optical patterns on two or three dimensional objects into device signals. The signals from the input devices 1304 are provided via various machine signal conductors (e.g., busses or network interfaces) and circuits to memory 1306.

The memory 1306 is typically what is known as a first or second level memory device, providing for storage (via configuration of matter or states of matter) of signals received from the input devices 1304, instructions and information for controlling operation of the CPU 1302, and signals from storage devices 1310.

Information stored in the memory 1306 is typically directly accessible to the CPU 1302 of the device. Signals input to the device cause the reconfiguration of the internal material/energy state of the memory 1306, creating in essence a new machine configuration, influencing the behavior of the digital apparatus 1300 by affecting the behavior of the CPU 1302 with control signals (instructions) and data provided in conjunction with the control signals.

Second or third level storage devices 1310 may provide a slower but higher capacity machine memory capability. Examples of storage devices 1310 are hard disks, optical disks, large capacity flash memories or other non-volatile memory technologies, and magnetic memories.

The CPU 1302 may cause the configuration of the memory 1306 to be altered by signals in storage devices 1310. In other words, the CPU 1302 may cause data and instructions to be read from storage devices 1310 in the memory 1306 from which may then influence the operations of CPU 1302 as instructions and data signals, and from which it may also be provided to the output devices 1308. The CPU 1302 may alter the content of the memory 1306 by signaling to a machine interface of memory 1306 to alter the internal configuration, and then converted signals to the storage devices 1310 to alter its material internal configuration. In other words, data and instructions may be backed up from memory 1306, which is often volatile, to storage devices 1310, which are often non-volatile.

Output devices 1308 are transducers which convert signals received from the memory 1306 into physical phenomenon such as vibrations in the air, or patterns of light on a machine display, or vibrations (i.e., haptic devices) or patterns of ink or other materials (i.e., printers and 3-D printers).

The network interface 1312 receives signals from the memory 1306 and converts them into electrical, optical, or wireless signals to other machines, typically via a machine network. The network interface 1312 also receives signals from the machine network and converts them into electrical, optical, or wireless signals to the memory 1306.

References to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple ones. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other.

"Logic" refers to machine memory circuits, non transitory machine readable media, and/or circuitry which by way of its material and/or material-energy configuration comprises control and/or procedural signals, and/or settings and values (such as resistance, impedance, capacitance, inductance, current/voltage ratings, etc.), that may be applied to influence the operation of a device. Magnetic media, electronic circuits, electrical and optical memory (both volatile and nonvolatile), and firmware are examples of logic. Logic specifically excludes pure signals or software per se (however does not exclude machine memories comprising software and thereby forming configurations of matter).

Those skilled in the art will appreciate that logic may be distributed throughout one or more devices, and/or may be comprised of combinations memory, media, processing circuits and controllers, other circuits, and so on. Therefore, in the interest of clarity and correctness logic may not always be distinctly illustrated in drawings of devices and systems, although it is inherently present therein.

The techniques and procedures described herein may be implemented via logic distributed in one or more computing devices. The particular distribution and choice of logic will vary according to implementation. Those having skill in the art will appreciate that there are various logic implementations by which processes and/or systems described herein can be effected (e.g., hardware, software, and/or firmware), and that the preferred vehicle will vary with the context in which the processes are deployed.

"Software" refers to logic that may be readily readapted to different purposes (e.g. read/write volatile or nonvolatile memory or media). "Firmware" refers to logic embodied as read-only memories and/or media. Hardware refers to logic embodied as analog and/or digital circuits. If an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware.

Hence, there are several possible vehicles by which the processes described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations may involve optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood as notorious by those within the art that each function and/or operation within such block diagrams, flowcharts, or examples can be implemented, individually and/or collectively, by a wide range of hardware, software, firmware, or virtually any combination thereof. Several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure.

In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, flash drives, SD cards, solid state fixed or removable storage, and computer memory.

In a general sense, those skilled in the art will recognize that the various aspects described herein which can be implemented, individually and/or collectively, by a wide range of hardware, software, firmware, or any combination thereof can be viewed as being composed of various types of "circuitry." Consequently, as used herein "circuitry" includes, but is not limited to, electrical circuitry having at least one discrete electrical circuit, electrical circuitry having at least one integrated circuit, electrical circuitry having at least one application specific integrated circuit, circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), circuitry forming a memory device (e.g., forms of random access memory), and/or circuitry forming a communications device (e.g., a modem, communications switch, or optical-electrical equipment).

Those skilled in the art will recognize that it is common within the art to describe devices and/or processes in the fashion set forth herein, and thereafter use standard engineering practices to integrate such described devices and/or processes into larger systems. That is, at least a portion of the devices and/or processes described herein can be integrated into a network processing system via a reasonable amount of experimentation.

What is claimed is:

1. A method of operating a vocal dosimeter, comprising:
receiving a first set of sensor data as sensor outputs through a sensor array comprising an acoustic sensor, a piezoelectric sensor, and an accelerometer;
operating an analog to digital converter to:
select one or more individual raw sensor waveforms from the sensor outputs through control of a selector;
duplicate each individual raw sensor waveform through control of a splitter;
store a duplicate of each individual raw sensor waveform in a raw data allocation of memory within a controlled memory data structure;
calculate quadratic mean of each individual raw sensor waveform through control of a normalizes;
generate normalized sensor waveforms by filtering for an amplitude range from the quadratic mean of each individual raw sensor waveform through control of a first band-pass filter; and
store the normalized sensor waveforms as normalized waveform data in a normalized data allocation of memory within the controlled memory data structure;
collecting recently stored normalized waveform data from each sensor of the sensor array and calculating a combined sensor amplitude through operation of an accumulator;
operating laryngeal activity detection logic to configure a vocalization filter with a vocalization threshold within a vocalization analysis window;
releasing the combined sensor amplitude from the vocalization filter to a second band-pass filter of a feedback logic in response to detecting the combined sensor amplitude exceeding the vocalization threshold for at least the duration of the vocalization analysis window;
operating the feedback logic to:
detect feedback activity in the combined sensor amplitude within a feedback initiation threshold range for at least the duration of a feedback initiation analysis window through control of the second band-pass filter;
generate a feedback control for the feedback activity in response to identifying a statistically similar vocalization amplitude in a vocal characteristic controlled memory data structure through control of an interpreter;
communicate the feedback control to a feedback controller; and
activating a user feedback device through operation of the feedback controller controlled by the feedback control.

2. The method of claim 1, further comprising:
storing a sample of the feedback activity in the combined sensor amplitude as a new vocalization amplitude in the vocal characteristic controlled memory data structure;

receiving a second set of sensor data at the sensor array following activation of the user feedback device;
operating feedback response logic to generate a feedback response sample by filtering out feedback device activation signatures from the combined sensor amplitude generated for the second set of sensor data; and
storing the sample of the feedback activity and the feedback response sample as a behavior modification dataset in the controlled memory data structure.

3. The method of claim 1, further comprising:
operating the laryngeal activity detection logic to:
retrieve the normalized waveform data for each of the sensors and calculate the combined sensor amplitude for the duration of a historical analysis time frame;
determine a statistical activity threshold for the duration of the historical analysis time frame;
compare the vocalization threshold to the statistical activity threshold; and
replace the vocalization threshold with the statistical activity threshold,
if the statistical activity threshold differs from the vocalization threshold.

4. The method of claim 1, wherein the vocalization analysis window is an overlapping sampling analysis window of the recently stored normalized waveform data.

5. The method of claim 1, wherein the feedback control is calculated as a linear inverse of the feedback activity.

6. A non-transitory computer-readable storage medium, the computer-readable storage medium including instructions that when executed by a computer, cause the computer to:
receive a first set of sensor data as sensor outputs through a sensor array comprising an acoustic sensor, a piezoelectric sensor, and an accelerometer;
operate an analog to digital converter to:
select one or more individual raw sensor waveforms from the sensor outputs through control of a selector;
duplicate each individual raw sensor waveform through control of a splitter;
store a duplicate of each individual raw sensor waveform in a raw data allocation of memory within a controlled memory data structure;
calculate quadratic mean of each individual raw sensor waveform through control of a normalizer;
generate normalized sensor waveforms by filtering for an amplitude range from the quadratic mean of each individual raw sensor waveform through control of a first band-pass filter; and
store the normalized sensor waveforms as normalized waveform data in a normalized data allocation of memory within the controlled memory data structure;
collect recently stored normalized waveform data from each sensor of the sensor array and calculating a combined sensor amplitude through operation of an accumulator;
operate laryngeal activity detection logic to configure a vocalization filter with a vocalization threshold within a vocalization analysis window;
release the combined sensor amplitude from the vocalization filter to a second band-pass filter of a feedback logic in response to detecting the combined sensor amplitude exceeding the vocalization threshold for at least the duration of the vocalization analysis window;
operate the feedback logic to:
detect feedback activity in the combined sensor amplitude within a feedback initiation threshold range for at least the duration of a feedback initiation analysis window through control of the second band-pass filter;
generate a feedback control for the feedback activity in response to identifying a statistically similar vocalization amplitude in a vocal characteristic controlled memory data structure through control of an interpreter;
communicate the feedback control to a feedback controller; and
activate a user feedback device through operation of the feedback controller controlled by the feedback control.

7. The computer-readable storage medium of claim 6 further comprising instructions that when executed by a computer, cause the computer to:
store a sample of the feedback activity in the combined sensor amplitude as a new vocalization amplitude in the vocal characteristic controlled memory data structure;
receive a second set of sensor data at the sensor array following activation of the user feedback device;
operate feedback response logic to generate a feedback response sample by filtering out feedback device activation signatures from the combined sensor amplitude generated for the second set of sensor data; and
store the sample of the feedback activity and the feedback response sample as a behavior modification dataset in the controlled memory data structure.

8. The computer-readable storage medium of claim 6, further comprising instructions that when executed by a computer, cause the computer to:
operate the laryngeal activity detection logic to:
retrieve the normalized waveform data for each of the sensors and calculate the combined sensor amplitude for the duration of a historical analysis time frame;
determine a statistical activity threshold for the duration of the historical analysis time frame;
compare the vocalization threshold to the statistical activity threshold; and
replace the vocalization threshold with the statistical activity threshold,
if the statistical activity threshold differs from the vocalization threshold.

9. The computer-readable storage medium of claim 6, wherein the vocalization analysis window is an overlapping sample analysis window of the recently stored normalized waveform data.

10. The computer-readable storage medium of claim 6, wherein the feedback control is calculated as a linear inverse of the feedback activity.

11. A computing apparatus, comprising:
a processor; and
a memory storing instructions that, when executed by the processor, configure the apparatus to:
receive a first set of sensor data as sensor outputs through a sensor array comprising an acoustic sensor, a piezoelectric sensor, and an accelerometer;
operate an analog to digital converter to:
select one or more individual raw sensor waveforms from the sensor outputs through control of a selector;
duplicate each individual raw sensor waveform through control of a splitter;
store a duplicate of each individual raw sensor waveform in a raw data allocation of memory within a controlled memory data structure;

calculate quadratic mean of each individual raw sensor waveform through control of a normalizer;

generate normalized sensor waveforms by filtering for an amplitude range from the quadratic mean of each individual raw sensor waveform through control of a first band-pass filter; and store the normalized sensor waveforms as normalized waveform data in a normalized data allocation of memory within the controlled memory data structure;

collect recently stored normalized waveform data from each sensor of the sensor array and calculating a combined sensor amplitude through operation of an accumulator;

operate laryngeal activity detection logic to configure a vocalization filter with a vocalization threshold within a vocalization analysis window;

release the combined sensor amplitude from the vocalization filter to a second band-pass filter of a feedback logic in response to detecting the combined sensor amplitude exceeding the vocalization threshold for at least the duration of the vocalization analysis window; and operate the feedback logic to:
  detect feedback activity in the combined sensor amplitude within a feedback initiation threshold range for at least the duration of a feedback initiation analysis window through control of the second band-pass filter;
  generate a feedback control for the feedback activity in response to identifying a statistically similar vocalization amplitude in a vocal characteristic controlled memory data structure through control of an interpreter;
  communicate the feedback control to a feedback controller; and
  activate a user feedback device through operation of the feedback controller controlled by the feedback control.

12. The computing apparatus of claim 11 wherein the instructions stored in the memory, when executed by the processor, configure the apparatus to:
  store a sample of the feedback activity in the combined sensor amplitude as a new vocalization amplitude in the vocal characteristic controlled memory data structure;
  receive a second set of sensor data at the sensor array following activation of the user feedback device;
  operate feedback response logic to generate a feedback response sample by filtering out feedback device activation signatures from the combined sensor amplitude generated for the second set of sensor data; and
  store the sample of the feedback activity and the feedback response sample as a behavior modification dataset in the controlled memory data structure.

13. The computing apparatus of claim 11, wherein the instructions stored in the memory, when executed by the processor, configure the apparatus to:
  operate the laryngeal activity detection logic to:
    retrieve the normalized waveform data for each of the sensors and calculate the combined sensor amplitude for the duration of a historical analysis time frame;
    determine a statistical activity threshold for the duration of the historical analysis time frame;
    compare the vocalization threshold to the statistical activity threshold; and
    replace the vocalization threshold with the statistical activity threshold,
  if the statistical activity threshold differs from the vocalization threshold.

14. The computing apparatus of claim 11, wherein the vocalization analysis window is an overlapping sample analysis window of the recently stored normalized waveform data.

15. The computing apparatus of claim 11, wherein the feedback control is calculated as a linear inverse of the feedback activity.

* * * * *